United States Patent [19]

Hieble

[11] Patent Number: 4,755,507

[45] Date of Patent: Jul. 5, 1988

[54] METHOD OF TREATING BENIGN PROSTATIC HYPERTROPHY

[75] Inventor: Jacob P. Hieble, Philadelphia, Pa.

[73] Assignee: SmithKline Beckman Corporation, Philadelphia, Pa.

[21] Appl. No.: 115,658

[22] Filed: Oct. 27, 1987

Related U.S. Application Data

[63] Continuation of Ser. No. 941,475, Dec. 15, 1986, abandoned.

[51] Int. Cl.⁴ .............................................. A61K 31/55
[52] U.S. Cl. .................................................. 514/213
[58] Field of Search ........................................ 514/213

[56] References Cited

U.S. PATENT DOCUMENTS 4,465,677  8/1984  DeMarinis et al. ................ 514/213
4,496,558  1/1985  DeMarinis et al. ................ 514/213

FOREIGN PATENT DOCUMENTS 80779     6/1983  European Pat. Off. ............ 514/213
108170A   5/1984  European Pat. Off. ............ 514/213

OTHER PUBLICATIONS

In Vitro Characterization of the α-Adrenoceptors in Human Prostate, European Journal of Pharmacology, 107 (1985), 111–117, J. P. Hieble et al.

Primary Examiner—Jerome D. Goldberg
Attorney, Agent, or Firm—Joseph A. Marlino; Stuart R. Suter; Alan D. Lourie

[57] ABSTRACT

Method of producing symptomatic relief in benign prostatic hypertrophy by administering 3-alkyl-6-halo-2,3,4,5-tetrahydro-1H-3-benzazepines.

3 Claims, No Drawings

METHOD OF TREATING BENIGN PROSTATIC HYPERTROPHY

This is a continuation of application Ser. No. 941,475 filed Dec. 15, 1986, now abandoned.

This invention relates to a method of treating benign prostatic hypertrophy by employing certain 3-alkyl-6-halo-2,3,4,5-tetrahydro-1H-3-benzazepines wherein halo is chloro or bromo. Advantageously the method of this invention employs 6-chloro-2,3,4,5-tetrahydro-3-methyl-1H-3-benzazepine in the symptomatic relief of benign prostatic hypertrophy.

Benign prostatic hypertrophy (BPH), often alternatively referred to as benign prostatic hyperplasia, is a condition characterized by a nodular enlargement of prostatic tissue resulting in obstruction of the urethra. The incidence of BPH is clearly age related. Based on an examination of autopsy specimens, a 30 percent incidence of benign hyperplasia was noted in prostates from men aged 60–69, and a 100 percent incidence from men over 90 (Randall and Hinman, 1983). This correlates with a 35 percent incidence of palpable prostatic enlargement during physical examination of men aged 60–69 (Lytton, 1983). It is estimated that half of all men over 65 have some prostatic enlargement, and at least one third of these will have clinical symptoms of BPH. In view of the continually increasing life span, the number of BPH patients and therefore the impact of this disease will continue to increase. Although BPH is currently treated primarily via surgical techniques, there is both clinical and experimental evidence to suggest that pharmacological management of this disease is possible and can delay or prevent the necessity of surgery in a significant percentage of patients.

It has been unexpectedly discovered that when pharmaceutical compositions containing 6-chloro-2,3,4,5-tetrahydro-3-methyl-1H-3-benzazepine (compound I) are internally administered to an animal, prostatic tone is reduced. The activity is demonstrated by the following in vivo studies.

An experimental model, using anesthetized dogs, was used to determine the effect of compound I on the tone in the prostatic portion of the uretha, as an indication of the combined tone of the urethra and the prostate surrounding it.

URETHRAL PRESSURE PROFILE DETERMINATION

In this procedure, analogous to that performed in human subjects, a catheter with a outflow port located on its side, near the closed tip, was inserted into the bladder through the urethra of an anesthetized, intact dog. The design of the catheter tip allows the determination of outflow resistance, and hence the pressure of the urethra on the catheter.

Once the catheter is in the bladder, perfusion of saline through the catheter is initiated. A pressure transducer in the line allows measurement of outflow pressure. While the catheter tip is in the bladder, outflow pressure equals zero. The catheter is slowly withdrawn from the bladder, through the urethra, continuously measuring outflow pressure. An increase in pressure is observed when the catheter tip passes into the urethra, and the highest pressure is recorded in the prostatic segment. Hence a single value, the peak urethral pressure, is recorded during each catheter withdrawal.

After a control determination, methoxamine is administered. Control experiments have shown that the increase in tone produced by methoxamine is stable for a least 20 minutes following this IV dose. Ten minutes after methoxamine dosing, the pressure profile is repeated; compound I is administered, and a third pressure profile is obtained, five minutes after compound I and ten minutes after the initial methoxamine dose.

| URETHRAL PRESSURE PROFILE, MALE ANESTHETIZED DOGS | |
|---|---|
| Treatment (n = 6) | Peak Urethral Pressure (mm Hg) |
| Control | 14 ± 1.8 |
| Methoxamine (0.1 mg/kg, IV) | 23 ± 2.1 |
| Methoxamine (0.1 mg/kg, IV) + Compound I (2.0 mg/kg, IV) | 6 ± 1.1 |

The pharmaceutical compositions used to carry out the method of treating BPH comprise a pharmaceutical carrier and, as the active ingredient, 6-chloro-2,3,4,5-tetrahydro-3-methyl-1H-3-benzazepine. The active ingredient will be present in the compositions in an effective amount to relieve BPH.

Preferably, the compositions contain the active ingredient, compound I, in an amount of from about 25 mg. to about 500 mg., advantageously from about 50 mg. to about 250 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of treating BPH according to this invention comprises administering to a subject, including humans, in an amount sufficient to relieve BPH 6-chloro-2,3,4,5-tetrahydro-3-methyl-1H-3-benzazepine or a nontoxic pharmaceutically acceptable salt of this compound.

Preferably, the compound is administered in conventional dosage unit forms prepared by combining an appropriate dose of the compound with standard pharmaceutical carriers.

Preferably, the active ingredient will be administered in a daily dosage regimen of from about 100 mg. to about 1000 mg., most preferably from about 200 mg. to about 500 mg. Advantageously, equal doses will be administered preferably two to four times per day. When the administration is carried out as described above, BPH is relieved.

The route of administration of the pharmaceutical compositions of this invention and in accordance with the methods of this invention is internal, either parenteral or preferably oral, in an amount to produce the desired biological activity.

The compound of this invention is known. The preparation of the compound and its pharmaceutically acceptable salts is set forth in U.S. Pat. No. 4,465,677.

The following examples are not limiting but are illustrative of the compounds of this invention.

EXAMPLE 1

| Ingredient | Amount |
| --- | --- |
| 6-Chloro-2,3,4,5-tetrahydro-3-methyl-1H—3-benzazepine hydrochloride | 150 mg. |
| Lactose | 350 mg. |

The ingredients are mixed and filled into a hard gelatin capsule.

One capsule is administered four times a day.

EXAMPLE 2

| Ingredients | Amounts |
| --- | --- |
| 6-Chloro-2,3,4,5-tetrahydro-3-methyl-1H—3-benzazepine hydrochloride | 200 mg. |
| Calcium sulfate dihydrate | 150 mg. |
| Sucrose | 25 mg. |
| Starch | 15 mg. |
| Talc | 5 mg. |
| Stearic Acid | 3 mg. |

The calcium sulfate dihydrate, sucrose and the benzazepine are thoroughly mixed and granulated with 10% gelatin solution. The wet granules are screened, dried and then mixed with the starch, talc and stearic acid, screened and compressed into a tablet.

One tablet is administered three times a day.

What is claimed is:

1. A method of treating benign prostatic hypertrophy which comprises administering to a human subject an amount sufficient to relieve benign prostatic hypertrophy of 6-chloro-2,3,4,5-tetrahydro-3-methyl-1H-3 benzazepine or a nontoxic pharmaceutically acceptable salt thereof.

2. The method of claim 1 which comprises administering a dosage unit containing from about 25 mg. to about 500 mg. of said benzazepine.

3. The method of claim 1 in which the benzazepine is in the form of its hydrochloride salt.

* * * * *